(12) United States Patent
Tang et al.

(10) Patent No.: US 9,629,905 B2
(45) Date of Patent: Apr. 25, 2017

(54) ***NEISSERIA MENINGITIDIS* FHBP VARIANT AND ITS USE FOR VACCINATION**

(71) Applicant: OXFORD UNIVERSITY INNOVATION LIMITED, Oxford (GB)

(72) Inventors: Christoph Tang, Oxford (GB); Susan Lea, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/423,047

(22) PCT Filed: Aug. 22, 2013

(86) PCT No.: PCT/GB2013/052215
§ 371 (c)(1),
(2) Date: Feb. 20, 2015

(87) PCT Pub. No.: WO2014/030003
PCT Pub. Date: Feb. 27, 2014

(65) Prior Publication Data
US 2015/0190494 A1    Jul. 9, 2015

(30) Foreign Application Priority Data

Aug. 23, 2012   (GB) .................................. 1215005.8

(51) Int. Cl.
*A61K 39/095* (2006.01)
*C07K 14/22* (2006.01)
*A61K 39/00* (2006.01)

(52) U.S. Cl.
CPC ............. *A61K 39/095* (2013.01); *C07K 14/22* (2013.01); *A61K 2039/552* (2013.01); *A61K 2039/575* (2013.01); *A61K 2039/70* (2013.01)

(58) Field of Classification Search
CPC .............. A61K 39/095; A61K 2039/70; A61K 2039/575; A61K 2039/552; C07K 14/22

USPC .............. 424/190.1; 435/325, 366; 530/405; 536/23.7
See application file for complete search history.

(56) References Cited

FOREIGN PATENT DOCUMENTS

| WO | 2006-081259 | 8/2006 |
|----|-------------|--------|
| WO | 2009-114485 | 9/2009 |

OTHER PUBLICATIONS

International Search Report and Written Opinion for related International Application No. PCT/GB2013/052215, issued Jan. 23, 2014.
Cartwright at al., "Neisseria meningitidis: Clinical Aspects," J. of Infection, 1997, 34: pp. 15-19.
Murphy et al., "Sequence Diversity of the Factor H Binding Protein Vaccine Candidate In Epidemiologically Relevant Strains Of Serogroup B Neisseria meningitidis," The Journal of Infectious Diseases, 2009: 200(3), pp. 379-389.
Masignani et al., "Vaccination against Neisseria meningitidis using three variants of the Lipoprotein GNA1870," The Journal of Experimental Medicine, 2003: 197(6), pp. 789-799.
Johnson et al., "Design and Evaluation of Meningococcal Vaccines through Structure-Based Modification of Host and Pathogen Molecules," CM.PLoS Pathog. 2012, 8(10) e1002981: pp. 1-13.
C0JFP2-C0JFP2_NEIME UniProt [online], [retrieved on Jun. 24, 2015]. Retrieved from the Internet: <URL: http://www.uniprot.org/uniprot/C0JFP2, 4 pages.

*Primary Examiner* — Padma V Baskar
(74) *Attorney, Agent, or Firm* — Porzio, Bromberg & Newman P.C.

(57) ABSTRACT

The invention relates to a modified V2 fHbp having increased stability over a wild type V2 fHbp; a modified V2 fHbp having an amino acid sequence with at least 85% identity to the sequence of Seq ID No: 1, wherein both $Ser^{137}$ and $Gly^{138}$ are mutated or both Val112 and Leu114 are mutated; immunogenic, pharmaceutical and vaccine compositions; nucleic acid and a host cell; and methods of use of such compositions.

15 Claims, 8 Drawing Sheets

Figure 1A:
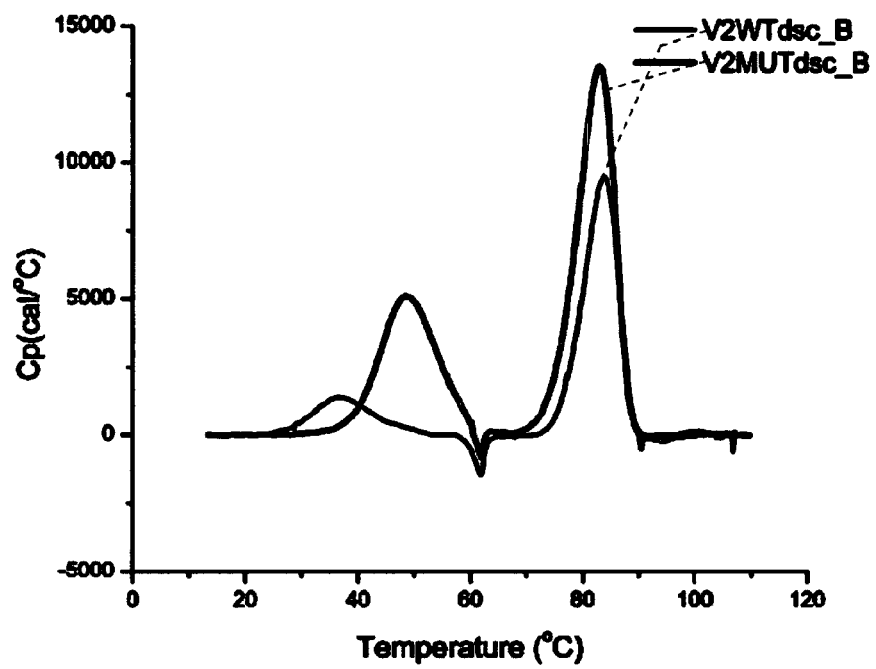

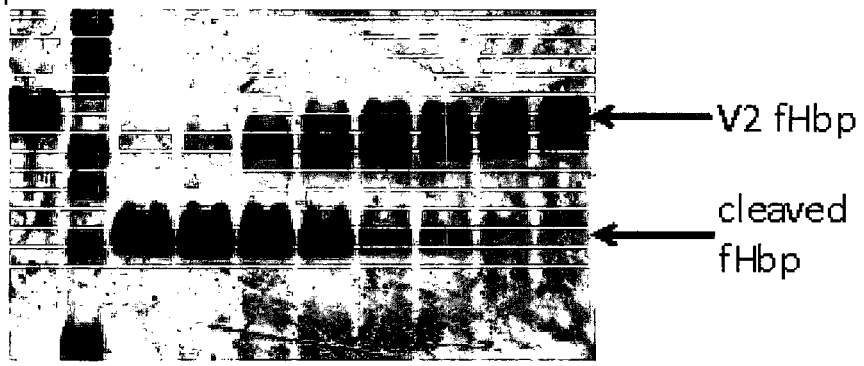
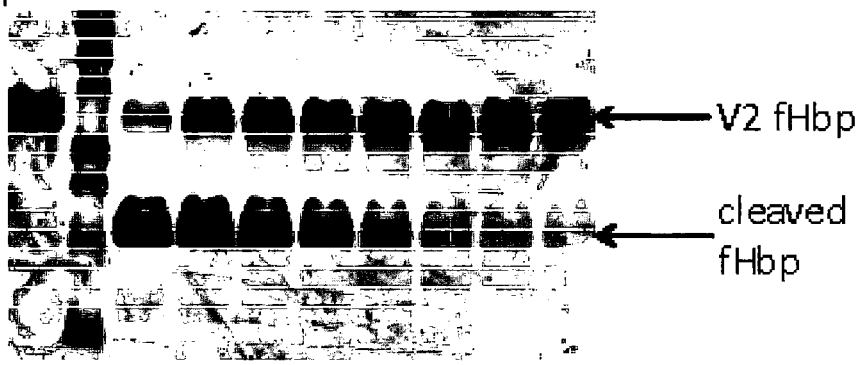
Figure 2

```
FHbp_V2 2.P22     5 CSSGGGGVAADIGAGLADALTAPLDHKDKSLQSLTLDQSVRKNEKLKLAAQGAEKTYGNG 65
FHbp_V2 2.P23     5 CSSGGGGVAADIGAGLADALTAPLDHKDKGLQSLTLDQSVRKNEKLKLAAQGAEKTYGNG 65
FHbp_V2 2.P25     5 CSSGGGGVAADIGAGLADALTTPLDHKDKSLQSLTLDQSVRKNEKLKLAAQGAEKTYGNG 65
FHbp_V2 2.P21     5 CSSGGGGVAADIGAGLADALTAPLDHKDKSLQSLTLDQSVRKNEKLKLAAQGAEKTYGNG 65
FHbp_V2 2.P16     5 CSSGGGGVAADIGAGLADALTAPLDHKDKSLQSLTLDQSVRKNEKLKLAAQGAEKTYGNG 65
FHbp_V2 2.P19     5 CSSGGGGVAADIGAGLADALTAPLDHKDKSLQSLTLDQSVRKNEKLKLAAQGAEKTYGNG 65
                    *********************:*******.******************************

FHbp_V2 2.P22    66 DSLNTGKLKNDKVSRFDFIRQIEVDGQLITLESGEFQIYKQDHSAVVALQIEKINNPDKI 125
FHbp_V2 2.P23    66 DSLNTGKLKNDKVSRFDFIRQIEVDGQLITLESGEFQIYKQDHSAVVALQIEKINNPDKI 125
FHbp_V2 2.P25    66 DSLNTGKLKNDKVSRFDFIRQIEVDGQTITLASGEFQIYKQNHSAVVALQIEKINNPDKI 125
FHbp_V2 2.P21    66 DSLNTGKLKNDKVSRFDFIRQIEVDGQLITLESGEFQIYKQDHSAVVALQIEKINNPDKI 125
FHbp_V2 2.P16    66 DSLNTGKLKNDKVSRFDFIRQIEVDGQLITLESGEFQIYKQDHSAVVALQIEKINNPDKI 125
FHbp_V2 2.P19    66 DSLNTGKLKNDKVSRFDFIRQIEVDGQLITLESGEFQIYKQDHSAVVALQIEKINNPDKI 125
                    *************************** *** *********:******************

FHbp_V2 2.P22   126 DSLINQRSFLVSGLGGEHTAFNQLPSGKAEYHGKAFSSDDPNGRLHYSIDFTKKQGYGRI 185
FHbp_V2 2.P23   126 DSLINQRSFLVSGLGGEHTAFNQLPSGKAEYHGKAFSSDDPNGRLHYSIDFTKKQGYGRI 185
FHbp_V2 2.P25   126 DSLINQRSFLVSGLGGEHTAFNQLPDGKAEYHGKAFSSDDPNGRLHYSIDFTKKQGYGRI 185
FHbp_V2 2.P21   126 DSLINQRSFLVSGLGGEHTAFNQLPGGKAEYHGKAFSSDDPNGRLHYSIDFTKKQGYGRI 185
FHbp_V2 2.P16   126 DSLINQRSFLVSGLGGEHTAFNQLPDGKAEYHGKAFSSDDAGGKLTYTIDFAAKQGHGKI 185
FHbp_V2 2.P19   126 DSLINQRSFLVSGLGGEHTAFNQLPSGKAEYHGKAFSSDDAGGKLTYTIDFAAKQGHGKI 185
                    *************************.**************..*:* *:***: ***:*:*

FHbp_V2 2.P22   186 EHLKTPEQNVELASAELKADEKSHAVILGDTRYGGEEKGTYHLALFGDRAQEIAGSATVK 245
FHbp_V2 2.P23   186 EHLKTPEQNVELASAELKADEKSHAVILGDTRYGGEEKGTYHLALFGDRAQEIAGSATVK 245
FHbp_V2 2.P25   186 EHLKTPEQNVELASAELKADEKSHAVILGDTRYGGEEKGTYHLALFGDRAQEIAGSATVK 245
FHbp_V2 2.P21   186 EHLKTPEQNVELASAELKADEKSHAVILGDTRYGSEEKGTYHLALFGDRAQEIAGSATVK 245
FHbp_V2 2.P16   186 EHLKTPEQNVELAAAELKADEKSHAVILGDTRYGSEEKGTYHLALFGDRAQEIAGSATVK 245
FHbp_V2 2.P19   186 EHLKTPEQNVELASAELKADEKSHAVILGDTRYGGEEKGTYHLALFGDRAQEIAGSATVK 245
                    *************:********************.*************************

FHbp_V2 2.P22   246 IREKVHEIGIAGKQ 259
FHbp_V2 2.P23   246 IREKVHEIGIAGKQ 259
FHbp_V2 2.P25   246 IREKVHEIGIAGKQ 259
FHbp_V2 2.P21   246 IREKVHEIGIAGKQ 259
FHbp_V2 2.P16   246 IGEKVHEIGIAGKQ 259
FHbp_V2 2.P19   246 IREKVHEIGIAGKQ 259
                    * ************
```

NEISSERIA MENINGITIDIS FHBP VARIANT AND ITS USE FOR VACCINATION

This application is a National Stage application under 35 U.S.C. §371, which claims benefit under 35 U.S.C. §119(a) of International Application No. PCT/GB2013/052215, filed Aug. 22, 2013, which claims priority to GB 1215005.8, filed Aug. 23, 2012, both of which are herein incorporated by reference.

The present invention relates to a factor H binding protein with improved stability, and in particular to the use of such a protein in immunogenic compositions for eliciting an immune response to pathogenic organisms. In particular the invention relates to immunogenic compositions for *Neisseria meningitidis*.

*Neisseria meningitidis* (meningococcus) is an encapsulated Gram-negative diplococcal bacterium that inhabits the nasopharynx/upper respiratory tract of humans and is an important cause of sepsis and meningitis. Carriage rates in the general population are usually around 10%. There are approximately 500,000 cases of meningococcal disease each year with around 50,000 deaths. In developed countries, the bacterium is a leading infectious cause of mortality among children, has important public health impacts during outbreaks in schools and universities, and can cause profound disability in survivors. Mortality for meningococcal septicaemia remains around 10%, and patients can develop neurological deficits and/or loss of limbs.

The *Neisseria meningitidis* organism is sensitive to several front line antibiotics. However, despite this, a significant number of patients diagnosed with meningococcal infection die of overwhelming disease or suffer serious complications. Mortality rates vary from 2-3% in cases of uncomplicated meningitis to 50% or more in cases of septic shock (Cartwright, K. A. and D. A. Ala'Aldeen (1997) J Infect 34:15-19).

The extremely rapid progression of meningococcal disease and non-specific early symptoms mean that vaccination is the best way to protect populations from the devastating consequences of meningococcal disease. Current vaccines only cover subsets of strains. Vaccines based on the polysaccharide capsule (which define the serogroup classification) are only effective against certain serogroups. This approach cannot be used against serogroup B disease which accounts for over 95% of clinical isolates in England and Wales, and predominates in developed countries. This is because the B capsule is identical to a modification on human NCAM-1. Outer membrane vesicle (OMVs) vaccines have been used successfully to prevent epidemics (most recently in New Zealand) but only confer protection against strains expressing the same variant of PorA (an outer membrane porin) as in the OMV. There is still no serogroup B vaccine that is suitable for routine immunisation schedules in Europe and the USA.

Another potential vaccine candidate is the factor H binding protein (fHbp) found on the surface of *Neisseria meningitidis*.

In healthy individuals, the activation of complement is precisely controlled through membrane-bound and soluble plasma-regulatory proteins including factor H (fH). Factor H is a 155 kDa protein composed of twenty domains (termed complement control protein repeats, or CCPs). Several pathogens have adapted to avoid complement-mediated killing by sequestering fH to their surface.

fHbp on *Neisseria meningitidis* is a 27 kDa lipoprotein that consists of two beta barrels (an N terminal barrel and a C terminal barrel) joined by a short amino acid linker. While charged carbohydrates on the surface of the vascular endothelium engage fH, charged amino acids in the fHbp bind fH at nanomolar affinities at the same site of this complement regulator.

Based on differences in the nucleotide and predicted amino acid sequences, fHbps from different *Neisseria meningitidis* strains have been categorised using several schemes. These include two subfamilies (A and B) (Murphy E, et al. (2009) The Journal of Infectious Diseases 200: 379-389) or three variant groups (V1, V2, and V3) (Masignani V, et al. (2003) The Journal of Experimental Medicine 197: 789-799), with subfamily A corresponding to V2 and V3, and subfamily B to V1 (which is the most abundant). Of note, fHbps belonging to the same variant group share over 85% amino acid similarity, and only 60-70% similarity between the three variant groups. fHbp is also an antigen that elicits serum bactericidal antibody responses in immunised individuals and is a key component of investigational vaccines for the prevention of meningococcal, in particular serogroup B, disease that are currently being evaluated in clinical trials. However immunisation with a protein belonging to one variant fHbp family generates a variant specific response, with no cross-reactivity to other variant groups. So a single fHbp will not provide universal protection against meningococcal disease, so immunisation with representatives from each of the three variants, V1, V2 and V3, is necessary for a broad based vaccine.

To date, no vaccine studies have included V2 fHbp even though strains expressing this variant account for around 20-30% of all isolates.

It is therefore an aim of the present invention to provide a novel V2 fHbp, and in particular a novel V2 fHbp that can be used in an immunogenic composition, wherein the novel protein may then be used to elicit an immune response against *Neisseria meningitidis*. The immune response elicited against *Neisseria meningitidis* may be protective.

According to a first aspect, the present invention provides a modified V2 fHbp having increased stability over a wild type (WT) V2 fHbp.

A modified V2 fHbp with increased stability may be defined as a protein in which the maximum value of the left hand peak in a differential scanning calorimetry ("DSC") analysis profile (corresponding to the N terminal beta barrel) is increased by at least about 5° C. compared with a wild-type fHbp protein.

The DSC profile for a WT V2 fHbp shows the independent unfolding of the two barrels, the N terminal barrel and the C terminal barrel. In a WT fHbp the peak representing unfolding of the C-terminal barrel shows melting at temperatures above 80° C. In contrast, in WT V2 fHbp the N-terminal barrel exhibits a much reduced melting point, between 30° C. and 40° C., indicating that this barrel readily unfolds. This unfolding of the N-terminal barrel in WT V2 fHbp may explain the increased susceptibility of the protein to proteolytic cleavage, as protease recognition sites in an unstable protein are accessible to the enzyme. In a modified V2 fHbp the maximum melting point of the N terminal barrel may be increased to between about 40° C. and about 60° C.

According to another aspect, the present invention provides a modified V2 fHbp having increased immunogenicity over a wild type (WT) V2 fHbp.

The sequence of six WT V2 fHbps is given in FIG. 3.

Reference herein to a modified V2 fHbp refers to a protein with an amino acid sequence that is not normally found in nature and instead is artificially produced and/or modified.

In one embodiment the modified V2 fHbp has one or more amino acid substitutions in the N terminal beta barrel. The amino acids which are mutated may be internally positioned in the beta barrel when the protein is folded. Not more than four consecutive amino acids may be mutated.

The amino acid substitution may be at one or more of the amino acids at position 30, 31, 37, 38, 41, 102, 107, 109, 132 and 133 in a protein of Seq ID No: 1 or a protein with at least 85%, 90%, 95% or more identity to Seq ID No: 1.

The substitution may be at one or more of Ser30, Leu31, Asp37, Gln38, Arg41, Asp102, Val107, Leu109, Ser132, Gly133.

The substitution may be at one or more of Ser30, Leu31, Asp37, Gln38, Arg41, Asp102, Val107, Leu109, Ser132, Gly133. The substitution may be at Ser30.

The modified V2 fHbp may have a mutation at one or both of $Ser^{132}$ and $Gly^{133}$. The modified V2 fHbp may have a mutation at both of $Ser^{132}$ and $Gly^{133}$. The modified V2 fHbp may have a mutation at $Ser^{132}$.

The modified V2 fHbp may have a mutation at Ser30, Asp102, Ser132 and Gly133. The modified V2 fHbp may have a mutation at Ser30, Leu109, Ser132 and Gly133. The modified V2 fHbp may have a mutation at Ser30, Asp102, Leu109, Ser132 and Gly133. The modified V2 fHbp may have a mutation at Ser30, Asp102, Val107, Leu109, Ser132 and Gly133. The modified V2 fHbp may have a mutation at both of Val107 and Leu109.

The modified V2 fHbp may have one or both of the following mutations, $Ser^{132}Gly$ and $Gly^{133}Asp$. The modified V2 fHbp may have both of the following mutations, $Ser^{132}Gly$ and $Gly^{133}Asp$. The modified V2 fHbp may have the following mutations, $Ser^{30}Gly$, $Asp^{102}Ser$, $Ser^{132}Gly$ and $Gly^{133}Asp$. The modified V2 fHbp may have the following mutations, $Ser^{30}Gly$, $Leu^{109}Phe$, $Ser^{132}Gly$ and $Gly^{133}Asp$. The modified V2 fHbp may have the following mutations, $Ser^{30}Gly$, $Asp^{102}Ser$, $Leu^{109}Phe$, $Ser^{132}Gly$ and $Gly^{133}Asp$. The modified V2 fHbp may have the following mutations, $Ser^{30}Gly$, $Asp^{102}Ser$, $Val^{107}Thr$, $Leu^{109}Phe$, $Ser^{132}Gly$ and $Gly^{133}Asp$. The modified V2 fHbp may have the following mutations, $Val^{107}Thr$ and $Leu^{109}Phe$. The modified V2 fHbp may have the following mutation, $Ser^{132}Gly$.

Alternatively, or additionally, one or more amino acid substitutions, insertions or deletion may be made in the linker region connecting the N and C terminal barrels. One or more amino acid substitutions, insertions or deletion may be made in amino acids 136 to 148 in a protein of Seq ID No: 1 or a protein with at least 85%, 90%, 95% or more identity to Seq ID No: 1.

Reference herein to a fHbp may refer to the factor H binding protein from *Neisseria meningitidis*.

The modified V2 fHbp may not be a chimeric protein. The modified V2 fHbp may not have beta barrels from different fHbp variants.

In this invention at least one modified V2 fHbp may be used as an antigen. The fHbp may be further modified to prevent, or reduce, binding of fH to the fHbp. The binding of fH to the fHbp following administration of the fHbp in a vaccine formulation to a subject may impair the success of the vaccine. First, the presence of fH on the fHbp may limit recognition of critical epitopes on the factor H binding protein by the host immune system. Antibodies generated against these epitopes may be both bactericidal and inhibit fH binding to bacteria rendering them sensitive to complement mediated lysis. Second, immune responses against the fHbp may also elicit responses against bound fH, in a manner similar to a hapten. This may lead to a potential, unwanted, autoimmune response. Finally, complement activation is involved in immune responses as complement proteins have adjuvant activity. Reduction of complement activation at the site of immunisation by recruitment of fH could impair the level of immunity obtained following vaccination.

According to another aspect the invention provides a modified V2 fHbp wherein both $Ser^{132}$ and $Gly^{133}$ are mutated, the mutations may comprise $Ser^{132}Gly$ and $Gly^{133}Asp$.

According to another aspect the invention provides a modified V2 fHbp wherein Ser30, Asp102, Ser132 and Gly133 are mutated, or wherein Ser30, Leu109, Ser132 and Gly133 are mutated, or wherein Ser30, Asp102, Leu109, Ser132 and Gly133 are mutated, or wherein Ser30, Asp102, Val102, Leu109, Ser132 and Gly133 are mutated, or wherein Val107 and Leu109 are mutated, or wherein Ser30 is mutated.

The mutations may comprise $Ser^{132}Gly$ and/or $Gly^{133}Asp$; or $Ser^{132}Gly$ and $Gly^{133}Asp$; or $Ser^{30}Gly$, $Asp^{102}Ser$, $Ser^{132}Gly$ and $Gly^{133}Asp$; or $Ser^{30}Gly$, $Leu^{109}Phe$, $Ser^{132}Gly$ and $Gly^{133}Asp$; or $Ser^{30}Gly$, $Asp^{102}Ser$, $Leu^{109}Phe$, $Ser^{132}Gly$ and $Gly^{133}Asp$; or $Ser^{30}Gly$, $Asp^{102}Ser$, $Val^{107}Thr$, $Leu^{109}Phe$, $Ser^{132}Gly$ and $Gly^{133}Asp$; or $Val^{107}Thr$ and $Leu^{109}Phe$; or $Ser^{132}Gly$.

The mutations may be in the N terminal beta barrel of the folded protein.

A V2 fHbp comprising both of the mutations $Ser^{132}Gly$ and $Gly^{133}Asp$ may be more stable than a V2 variant which does not.

The modified fHbp may have at least 80%, 85%, 90%, 95% or more sequence identity with a sequence of FIG. 3, such as the sequence of Seq ID No: 1, but is modified in at least one position which increases the protein stability. The modification may be a different amino acid.

Percentage sequence identity is defined as the percentage of amino acids in a sequence that are identical with the amino acids in a provided sequence after aligning the sequences and introducing gaps if necessary to achieve the maximum percent sequence identity. Alignment for the purpose of determining percent sequence identity can be achieved in many ways that are well known to one of ordinary skill in the art, and include, for example, using BLAST (National Center for Biotechnology Information Basic Local Alignment Search Tool).

Variations in percent identity may be due, for example, to amino acid substitutions, insertions or deletions. Amino acid substitutions may be conservative in nature, in that the substituted amino acid has similar structural and/or chemical properties, for example the substitution of leucine with isoleucine is a conservative substitution.

According to a further aspect, the invention provides an immunogenic composition comprising a modified V2 fHbp according to any aspect of the invention.

An immunogenic composition is a composition that is capable of eliciting an immune response to the modified V2 fHbp when the composition is administered to a subject. The subject may be a human or non-human animal. The subject may be a mammal.

The immune response elicited by the composition of the invention may affect the ability of *N. meningitidis* to infect an immunised human. The ability of *N. meningitidis* to infect a human immunised with the composition of the invention may be impeded or prevented. This may be achieved in a number of ways. The immune response elicited may recognise and destroy *N. meningitidis*. Alternatively, or additionally, the immune response elicited may impede or prevent replication of *N. meningitidis*. Alternatively, or additionally, the immune response elicited may impede or prevent *N. meningitidis* causing disease in the human or non-human animal. The composition may elicit a bactericidal antibody response effective against bacterial strains expressing the V2 fHbp. The immune response elicited by the composition of the invention may be equivalent or greater than an immune response elicited by wild type V2 fHbp.

The modified fHbp may be recombinantly produced (e.g. from a genetically-engineered expression system) or be a synthetic product, for example produced by in vitro peptide synthesis or in vitro translation.

The composition of the invention may also comprise a further one or more antigens, in addition to the modified V2 fHbp. The further antigens may also be derived from *N. meningitidis* and may be capable of eliciting an immune response directed to *N. meningitidis*.

The composition may be used to elicit/produce a protective immune response when administered to a subject. The protective immune response may cause *N. meningitidis* to be killed upon infecting the subject, or it may prevent or inhibit *N. meningitidis* from replicating and/or from causing disease.

The composition may be used as a prophylactic or a therapeutic vaccine directed to *N. meningitidis*.

According to a further aspect, the invention provides a pharmaceutical composition comprising a modified V2 fHbp according to the invention and a pharmaceutically acceptable carrier or excipient.

The pharmaceutical composition may be capable of producing a protective immune response to *N. meningitidis*.

The phrase "producing a protective immune response" as used herein means that the composition is capable of generating a protective response in a host organism, such as a human or a non-human mammal, to whom it is administered. A protective immune response may protect against subsequent infection by *N. meningitidis*. The protective immune response may eliminate or reduce the level of infection by reducing replication of *N. meningitidis* or by affecting the mode of action of *N. meningitidis* to reduce disease.

Suitable acceptable excipients and carriers may include solid or liquid carriers. Suitable liquid carriers include water and saline. The proteins of the composition may be formulated into an emulsion or they may be formulated into biodegradable microspheres or liposomes.

The composition may further comprise an adjuvant. Suitable adjuvants may include Freund's Incomplete Adjuvant (for use in animals), and metal salts, such as aluminium or calcium salts.

The composition may also comprise polymers or other agents to control the consistency of the composition, and/or to control the release of the antigen/secreted protein from the composition.

The composition may also comprise other agents such as diluents, which may include water, saline, glycerol or other suitable alcohols etc; wetting or emulsifying agents; buffering agents; thickening agents for example cellulose or cellulose derivatives; preservatives; detergents, antimicrobial agents; and the like.

The active ingredients in the composition may be greater than 50% pure, usually greater than 80% pure, often greater than 90% pure. The active ingredients may be greater than 95%, 98% or 99% pure. With active ingredients approaching 100% pure, for example about 99.5% pure or about 99.9% pure, being used most often.

The composition of the present invention may be used as vaccine against infections caused by *N. meningitidis*. The composition may be used as a vaccine directed to meningitis or other invasive meningococcal diseases including septicaemia or septic shock. The vaccine may be administered prophylactically to those at risk of exposure to *N. meningitidis*, and/or therapeutically to persons who have already been exposed to *N. meningitidis*.

If the composition is used as a vaccine, the composition may comprise an immunologically effective amount of antigen wherein the composition comprises at least one modified V2 fHbp. An "immunologically effective amount" of an antigen is an amount that when administered to an individual, either in a single dose or in a series of doses, is effective for treatment or prevention of infection by *N. meningitidis*. This amount will vary depending upon the health and physical condition of the individual to be treated and on the antigen. Determination of an effective amount of an immunogenic or vaccine composition for administration to an organism is well within the capabilities of those skilled in the art.

A composition according to the invention may be for oral, systemic, parenteral, topical, mucosal, intramuscular, intravenous, intraperitoneal, intradermal, subcutaneous, intranasal, intravaginal, intrarectal, transdermal, sublingual, inhalation or aerosol administration.

The composition may be arranged to be administered as a single dose or as part of a multiple dose schedule. Multiple doses may be administered as a primary immunisation followed by one or more booster immunisations. Suitable timings between priming and boosting immunisations can be routinely determined.

A composition according to the invention may be used in isolation, or it may be combined with one or more other immunogenic or vaccine compositions, and/or with one or more other therapeutic regimes.

Compositions of the invention may be able to induce a serum bactericidal antibody responses and elicit antibodies which mediate opsonphagocytosis after being administered to a subject. These responses can be conveniently measured in mice and the results are a standard indicator of vaccine efficacy.

The compositions of the invention may also, or alternatively, be able to elicit an immune response which neutralises bacterial proteins or other molecules, thereby preventing them from having their normal function and preventing or reducing disease progression without necessarily destroying the pathogenic organism/bacteria, in this case to *N. meningitidis*.

A composition according to the invention may also comprise a further one or more antigens, in addition to the modified V2 fHbp. The further antigens may also be derived from *N. meningitidis* and may be capable of eliciting an immune response directed to *N. meningitidis*. The further antigens may include one or more of a V1 fHbp and a V3 fHbp.

According to a further aspect, the present invention provides the use of one or more modified V2 fHbps in the preparation of a medicament for eliciting an immune response. The medicament may be used for the prophylactic or therapeutic vaccination of subjects against *N. meningitidis*. The medicament may be a prophylactic or a therapeutic vaccine. The vaccine may be for meningitis, septicaemia and/or septic shock caused by *N. meningitidis*.

According to a yet further aspect, the invention provides a composition comprising one or more modified V2 fHbp for use in generating an immune response to *N. meningitidis*.

The immune response may be prophylactic or therapeutic. The composition may be for use as a vaccine.

According a still further aspect, the present invention provides a method of protecting a human or non-human animal from the effects of infection by *N. meningitidis* comprising administering to the human or non-human animal a composition according to any aspect of the invention or a modified occurring V2 fHbp according to any aspect of the invention. The composition may be a vaccine.

According to another aspect, the invention provides a method for raising an immune response in a human or non-human animal comprising administering a pharmaceutical composition according to the invention to the human or non-human animal. The immune response may be protective. The method may raise a booster response in a patient that has already been primed. The immune response may be prophylactic or therapeutic.

One way to check the efficacy of a therapeutic treatment comprising administration of a composition according to the invention involves monitoring for *N. meningitidis* infection after administration of the composition. One way to check the efficacy of a prophylactic treatment comprising administration of a composition according to the invention involves monitoring immune responses to *Neisseria meningitidis* after administration of the composition.

According to another aspect, the invention provides the use of one or more modified V2 fHbps in the preparation of a medicament for use in the immunisation of human or non-human mammals against infection by *N. meningitidis*.

According to a further aspect the invention provides a kit for use in inducing an immune response in an organism, comprising an immunogenic or vaccine composition according to the invention and instructions relating to administration.

In addition to their potential use as vaccines, compositions according to the invention may be useful as diagnostic reagents and as a measure of the immune competence of a vaccine.

According to another aspect the invention provides a nucleic acid encoding a modified V2 fHbp according to the invention.

According to a still further aspect the invention provides a host cell containing the above nucleic acid.

One of ordinary skill in the art will appreciate that any of the optional features discussed above can be applied to any of the aspects or embodiments of the invention.

Embodiments of the present invention will now be described, merely by way of example, with reference to the following figures and examples.

Figure 1B:
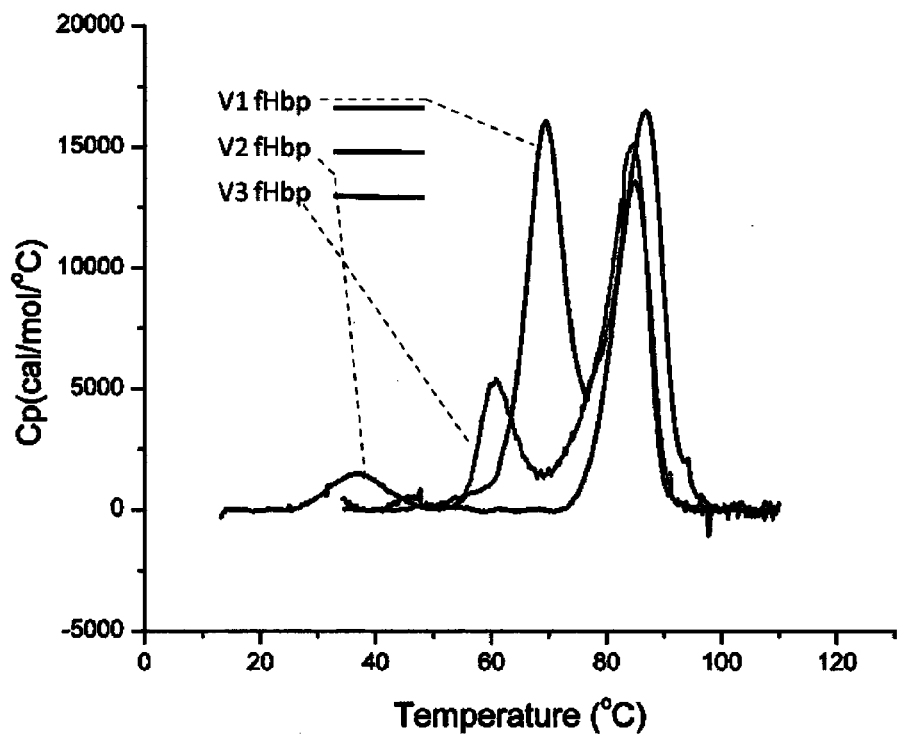

FIG. 1A—DSC of a wild-type V2 protein (green/dark trace) and the modified fHbp V2MUT (red/light trace, with the modifications Ser$^{132}$Gly and Gly$^{133}$Asp) which contains two amino acid changes in the N terminal barrel. The two peaks for each protein represent unfolding of the N terminal barrel (left hand peak, at lower temperatures) and C terminal barrel (right hand peak). Modification of the V2 protein increases the peak associated with the C terminal barrel and shifts the peak to higher temperatures. FIG. 1B—DSC of V1 (red line), V2 (blue line) and V3 (green line) fHbp showing unfolding of the C-terminal barrel at around 80° C. for all variants, and the N-terminal barrel at lower temperatures.

FIG. 2—Sensitivity of the wild-type (V2WT) and stabilised (V2MUT) V2 protein to proteolytic cleavage. Proteins were incubated in the presence of the protease for increasing concentrations of trypsin (right to left) and analysed by SDS:PAGE.

FIG. 3—shows sequences of some WT V2 fHbps, identical amino acids are shown with asterisks. FHbp_V2_peptide_22 is referred to herein as Seq ID No: 1. FHbp_V2_peptide_23 is referred to herein as Seq ID No: 2. FHbp_V2_peptide_25 is referred to herein as Seq ID No: 3. FHbp_V2_peptide_21 is referred to herein as Seq ID No: 4. FHbp_V2_peptide_16 is referred to herein as Seq ID No: 5. FHbp_V2_peptide_19 is referred to herein as Seq ID No: 6. In all sequence the N terminal beta barrel spans amino acids numbers 15 to 136, and amino acids residues 136 to 148 represent a linked between the N and C terminal beta barrels.

Figure 4:

FIG. 4—shows a cartoon representation of V1 fHbp structure with the six V2 fHbp stabilising amino acid changes mapped on it. Figure created using PyMol based on pdb entry 2W80.

Figure 5A:
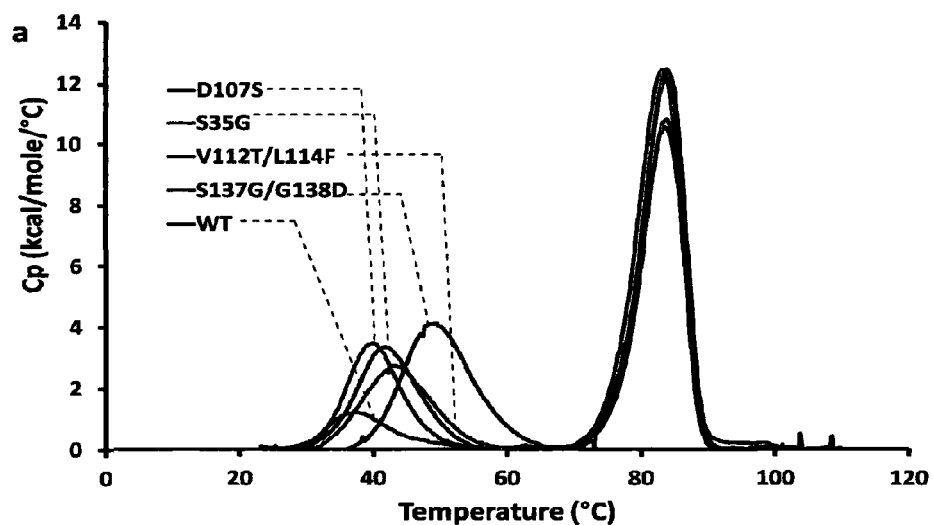
Figure 5B:
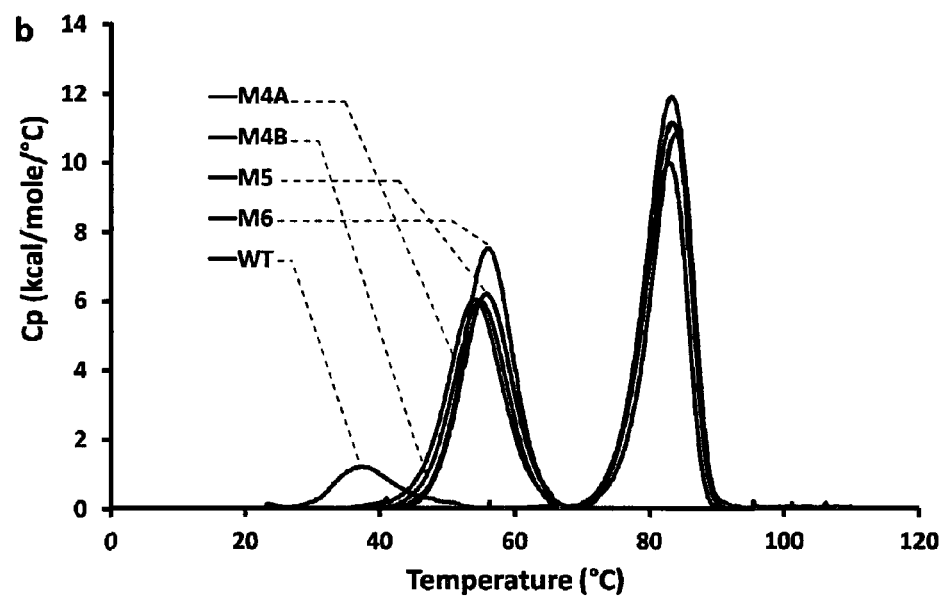
Figure 5C:
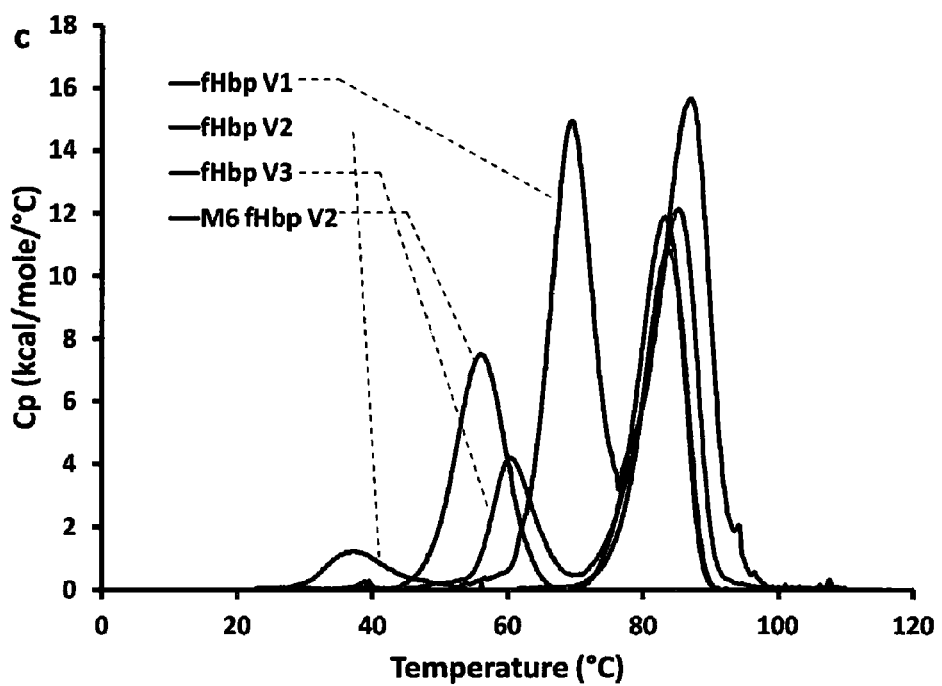

FIG. 5—illustrates the effect of stabilising mutations in V2 fHbp. The heat capacity (Cp) of V2 fHbp mutants was measured by DSC. FIG. 5A—V2 fHbp with single and double amino acid substitutions. FIG. 5B—Four combinations of mutations that showed the greatest increase in stability. FIG. 5C—M6 compared to WT V1, V2 and V3 fHbp.

Figure 6:
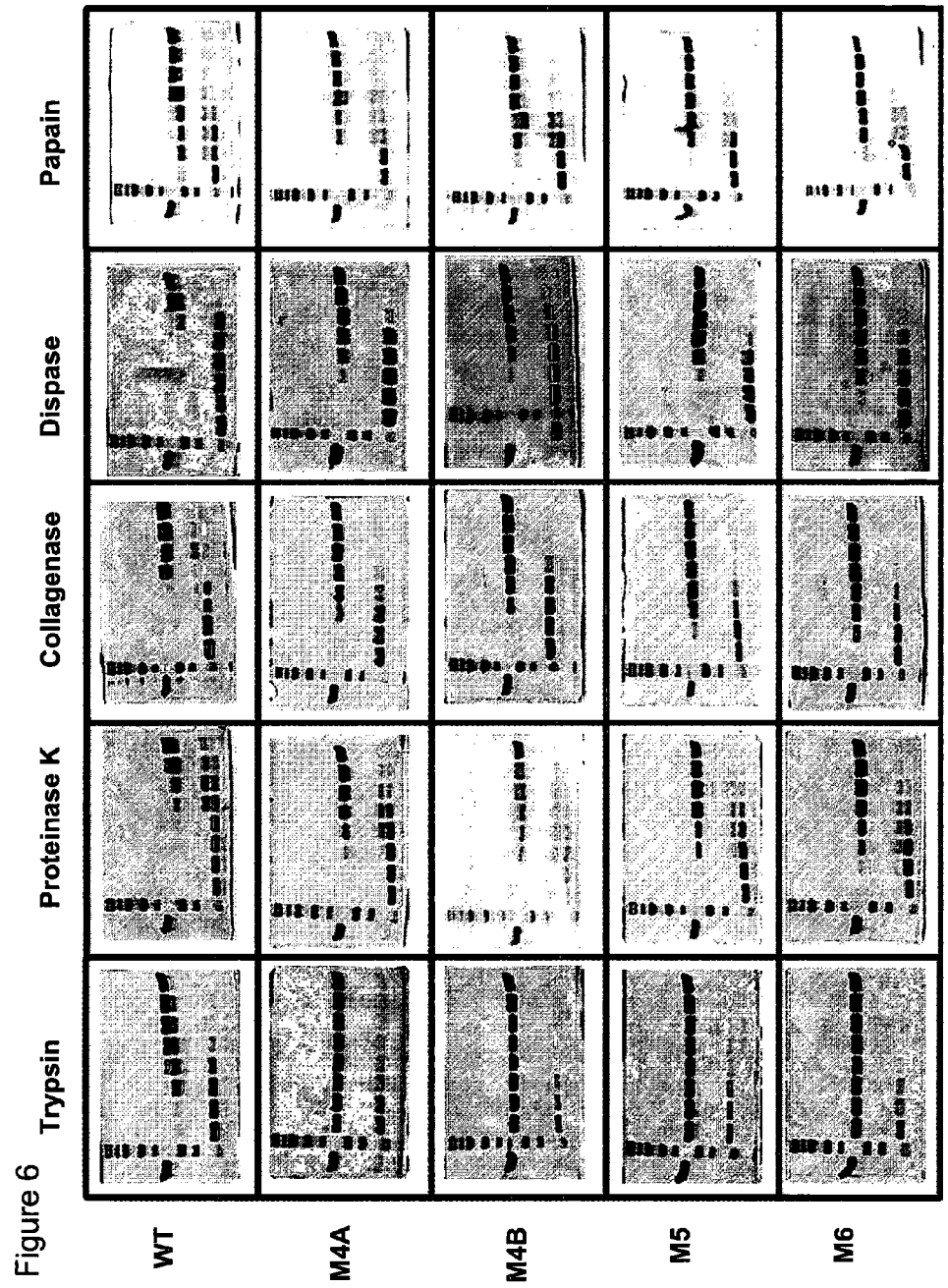

FIG. 6—shows the susceptibility of stabilised V2 fHbps to protease digestion. SDS:PAGE stained with Coomassie blue of V2 fHbp following protease treatment in serial dilutions (lanes 3-10).

Figure 7:
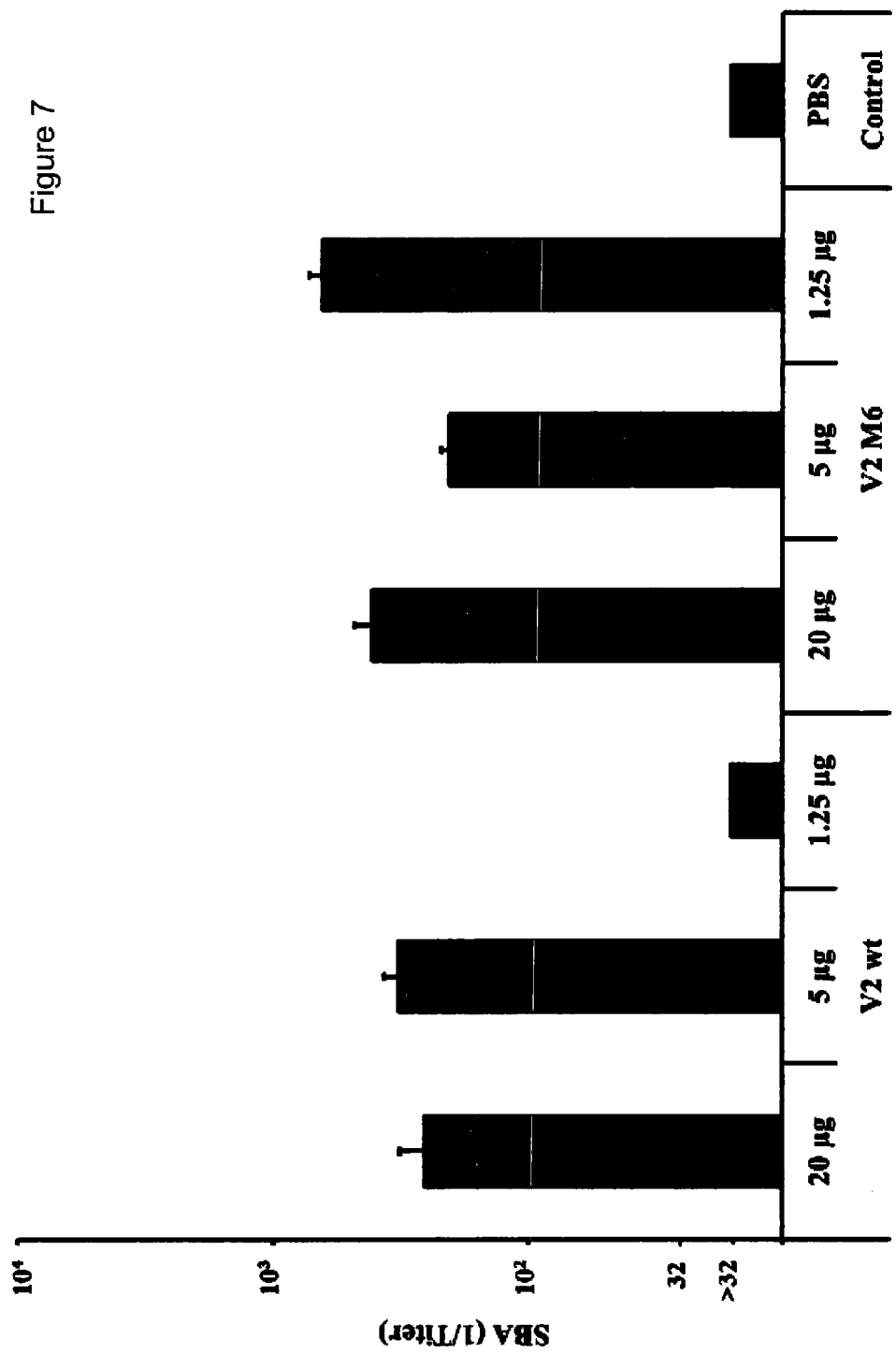

FIG. 7—shows SBA titres of mice. Animals received different doses of the wild-type and M6 V2 fHbp (shown) on three occasions, and SBA was determined for pooled sera against a clinical isolate expressing V2 fHbp. Error bars: SD of assays performed in triplicate.

The data presented herein demonstrates the inherent instability of the WT V2 fHbp, in particular the instability of the N terminal beta barrel. This instability demonstrates its unsuitability for vaccine development, both for reliable antigen product and because several bactericidal antibodies are known to require conformational epitopes involving both the N and C terminal beta barrels.

Further more, the data also demonstrates that by mutating the amino acid sequence of the N terminal beta barrel the stability of the V2 fHbp can be significantly increased. The stabilised protein can then be used as an immunogen.

Stable Modified V2 fHbp

WT V2 fHbp with the sequence of FIG. 3, Seq ID No: 1, was mutated using PCR to change the amino acid at position 132 from serine to glycine and the amino acid a position 133 from glycine to aspartic acid. Both of these mutations are in the N terminal beta barrel of the protein. The modified protein produced is referred to herein as V2MUT.

The stability of the mutant produced was assessed by differential scanning calorimetry (DSC, FIG. 1) and by susceptibility to protease cleavage (FIG. 2).

FIG. 1 clearly demonstrates that the V2MUT protein has dramatically increase stability compared to the wild type protein. The N terminal barrel has a mean melting temperature of around 50° C., compared to about 35° C. for the wild type protein. No significant change in stability was seen in the C terminal barrel of the V2MUT protein.

The improved stability of the mutant V2 fHbp is further supported by the results of proteolytic cleavage study (FIG. 2). More cleavage product (lower band) is generated when the wild-type protein is incubated with protease than when the V2MUT protein is treated under identical conditions. This demonstrates that V2MUT is less susceptible to digestion, due to increased stability of the protein.

Efficacy of V2MUT as an Immunogen

Female six to eight-week-old BALB/c mice (Charles Rivers) are immunised with antigens (20 µg of WT V2 fHbp or V2MUT fHbp) with aluminium hydroxide adsorbed by spinning the mixture for one hour at room temperature. Immunogens are given intraperitoneally (transgenic mice) on days 0, 21 and 35; sera are collected on day 49. In immunisation studies with C57Bl/6 transgenic mice, antigens are given intraperitoneally to twelve to sixteen-weeks-old mice on days 0, 21 and 35, and whole blood collected by terminal anaesthesia and cardiac puncture from the mice on day 49. All procedures are conducted in accordance with Home Office guidelines.

Wells of ELISA plates (Nunc) are coated with mutant V2 (V2MUT) fHbp (100 ng) overnight at 4° C., washed, blocked for one hour with 3% normal goat serum diluted in PBS-T, then sera added at a range of dilutions. Binding is detected using goat anti-mouse HRP-conjugated IgG (Dako, 1 in 1,000) and incubated for one hour at room temperature. The substrate (ONPG, Sigma) is added to wells, the reaction is stopped with 3N HCl, and the A492 read with a Multiskan photometer (Thermo Scientific).

For serum bactericidal assays, N. meningitidis MC58 is re-suspended in SBA assay buffer (0.1% glucose in PBS) to a final concentration of 5×104 CFU/ml and mixed with an equal volume of human complement. Control wells are also prepared containing bacteria without serum or without complement. Sera are pooled from groups of non-transgenic mice (n>8), and immunisations repeated on two or three occasions for each antigen; for transgenic mice, sera are tested from individual animals. Following incubation, 10 µl from each well is plated onto solid media, and the number of surviving bacteria is determined after overnight growth. The bactericidal activity is expressed as the reciprocal of the highest dilution of sera required to kill more than 50% of bacteria.

Mice immunised as described above with the WT and mutant (V2MUT) V2 fHbp will demonstrate that the stabilised modified occurring V2 fHbp (V2MUT) is significantly more immunogenic that the WT fHbp.

Further Studies

V2 fHbp is not included in either of the two vaccines currently undergoing clinical trials. This could be because its inherent instability prevents it from being a good vaccine candidate (Johnson et al, 2012). Vaccine coverage could be improved by including V2 fHbps as 20-30% of N. meningitidis isolates express V2 fHbps. In order to do this V2 fHbp would need to be stabilised.

Previously, we found that a region of V2 fHbp is involved in its susceptibility to trypsin digestion. This region was used as the site for a large scale screen to identify mutations that increase V2 fHbp's stability. Amino acids in this region were mutated to their equivalent residue in V1 Six fHbp. mutations (S32G, D102S, V107T, L109F, S132G, G133D) were identified that enhance the stability of V2 fHbp (FIG. 4). These six mutations are all in the N terminal barrel of fHbp.

To identify the most effective combination of changes for stabilising V2 fHbp, 13 V2 fHbps were expressed (Table 1) with different combinations of these six amino acid changes.

TABLE 1

Stabilised V2 fHbps. The stability of these V2 fHbp mutants was analysed. The table contains the name of the mutant and the amino acid changes made in WT V2 fHbp.

| Name of mutant | Amino acid changes |
| --- | --- |
| M4A | S30G/D102S/S132G/G133D |
| M4B | S30G/L109F/S132G/G133D |
| M5 | S30G/D102S/L109F/S132G/G133D |
| M6 | S30G/D102S/V107T/L109F/S132G/G133D |
| V107T | V107T |
| D102S | D102S |
| L109F | L109F |
| S30G | S30G |
| S132G/G133D | S132G/G133D |
| V107T/L109F | V107T/L109F |
| D102S/L109F | D102S/L109F |
| S30G/D102S | S30G/D102S |
| S30G/D102S/L109F | S30G/D102S/L109F |

The stability of the V2 fHbps was assessed by Differential Scanning Calorimetry (DSC) to determine the melting temperatures of the two β barrels. The N terminal β barrel of WT fHbp melts first ($T_m1$) at 37.30° C., while the C terminal β barrel melts ($T_m2$) at 83.06° C. This indicates that the N terminal barrel is less stable than the C terminal barrel. The DSC profiles were determined for all thirteen mutants. The DSC profiles of four mutants, that contain the six mutations in single or double combinations, are shown in FIG. 5A. The increased $T_m1$ value relative to WT V2 fHbp indicates an increase in stability of the N terminal barrel. There was no change in the $T_m2$ values between the WT and the mutants, showing there is no change in the stability of the C terminal barrel. The DSC profiles of all thirteen mutants (not shown) showed that the four mutants that had the greatest increase in stability were: M4A, M4B, M5 and M6 (FIG. 5B). Their $T_m1$ values (Table 2) had the largest increase, indicating greater stability of their N terminal barrel. From DSC M6 was more stable than either M4A, M4B or M5 with a $T_m1$ of 55.96° C. for M6 compared with 54.03, 54.79, 55.46° C. for M4A, M4B and M5 respectively. The $T_m1$ value of M6 is lower than the $T_m1$ values of WT V1 and V3 fHbp (FIG. 5C), indicating that its N terminal barrel is less stable.

TABLE 2

Melting temperature of the N and C teminal β-barrels ($T_m1$ and $T_m2$, respectively) and the enthalpy of melting of the N and C terminal β-barrels (ΔH1 and ΔH2, respectively) of stabilised V2 fHbp mutants in comparison with WT V2 fHbp.

| mutant | Tm1 (° C.) | ΔH1 (kJ) | Tm2 (° C.) | ΔH2 (kJ) |
| --- | --- | --- | --- | --- |
| WT | 37.30 | 24.6 | 83.06 | 101.7 |
| L109F | 36.06 | 32.7 | 83.06 | 114.6 |
| D102S/L109F | 39.35 | 44.3 | 82.95 | 96.8 |
| V107T | 39.95 | 22.7 | 83.00 | 107.6 |
| D102S | 40.23 | 48.4 | 83.14 | 109.5 |
| S30G | 42.14 | 49.2 | 83.20 | 111.2 |
| S30G/D102S/L109F | 42.50 | 50.5 | 82.90 | 101.8 |
| V107T/L109F | 43.81 | 44.6 | 83.08 | 101.2 |
| S30G/D102S | 47.26 | 66.2 | 83.05 | 115.7 |
| S132G/G133D | 49.56 | 58.1 | 82.54 | 111.5 |
| M4A | 54.03 | 70.6 | 82.56 | 104.6 |
| M4B | 54.79 | 70.4 | 82.57 | 105.0 |
| M5 | 55.46 | 76.2 | 82.40 | 100.9 |
| M6 | 55.96 | 79.6 | 82.56 | 108.7 |

Selecting the Most Stable V2 fHbp

To further define the stability of the four most stable V2 fHbp mutants, protease digestion assays were performed.

Five different proteases were used: trypsin, proteinase K, collagenase, dispase and papain. All four mutants showed enhanced resistance to protease digestion compared to WT V2 fHbp. M6 was the least susceptible to protease digestion with collagenase, proteinase K, dispase, and papain (FIG. 6). All four mutants (M4A, M4B, M5 and M6) showed enhanced resistance to trypsin digestion in comparison with WT V2 fHbp, but there was no clear difference between them with this protease. For proteinase K, dispase and papain, M6 showed the most resistance to protease digestion, followed by M5, consistent with V2 fHbp mutants containing more mutations being more stable. M4A and M4B show intermediate levels of susceptibility. In summary both DSC and protease digestion indicate that the V2 fHbp mutant with six stabilising amino acid changes (M6) is the most stable.

fH Binding to Stable V2 fHbps

To determine the effect of stabilising V2 fHbp on fH binding, SPR was carried out using the four most stable V2 fHbp mutants immobilised on the sensor chip and flowing $fH_{67}$ over them. $K_d$ values for $fH_{67}$ binding to the stable V2 fHbps were calculated from the sensogram ($fH_{67}$ binding to WT V2 fHbp shown in Appendix 3a) and compared to $fH_{67}$ binding to WT V2 fHbp (Table 3). The $K_d$ values for M4A, M4B and M5 were between two and four fold higher (indicating a lower binding affinity) than for WT V2 fHbp, whilst the $K_d$ for M6 is almost twenty fold higher. The decrease in $fH_{67}$ binding of M6 is potentially beneficial as this will help to produce a stable V2 fHbp vaccine candidate that does not bind fH.

TABLE 3 fH binding to V2 fHbps: table of $K_d$ values and relative $K_d$ values for the V2 fHbps in comparison with WT V2 fHbp. Mean ± standard deviation of two determinations.

| Protein | Average $K_d$ (nM) | Relative $K_d$ |
|---------|--------------------|----------------| 
| WT      | 3.18 ± 0.11        | 1.00           |
| M4A     | 7.60 ± 0.17        | 2.39           |
| M4B     | 12.50 ± 0.21       | 3.92           |
| M5      | 12.20 ± 0.71       | 3.84           |
| M6      | 61.30 ± 6.86       | 19.29          |

Immunogenicity of M6 in Comparison with WT V2 fHbp

The immunogenicity of M6 was compared with WT V2 fHbp. Non transgenic mice were immunised with three different amounts of both WT and M6 V2 fHbp in order to establish a dose response. To assess the immune response, the serum bactericidal activity (SBA) of sera from immunised mice was determined. The SBA is a correlate of protection against meningococcal disease. The results show that M6 V2 fHbp has equivalent or better immunogenicity than the wild-type protein because SBA is still detected in mice vaccinated with the lowest dose of M6 V2 fHbp, while mice receiving the same amount of the wild-type protein fail to elicit SBA (FIG. 7).

Materials and Methods

Bacterial Growth and Western Analysis

*N. meningitidis* was grown in 5% $CO_2$ on Brain Heart Infusion (BHI) agar plates with Levanthal's supplement, and *Escherichia coli* propagated in LB liquid medium with shaking at 200 r.p.m. or on LB agar plates (1.5% agar wt/vol). Whole cell lysates were prepared of *N. meningitidis* grown overnight on solid media then re-suspended in PBS. The concentration of bacteria was determined by measuring the optical density at 260 nm of bacterial lysates in 1% SDS/0.1M NaOH [15] and adjusted to 1×109 CFU/ml, and re-suspended with an equal volume of 2×SDS-PAGE loading buffer (100 mM Tris-HCl pH 6.8, 20 µM β-mercaptoethanol, 4% SDS, 0.2% bromophenol blue, 20% glycerol), and boiled for 10 minutes; polyacrylamide gels which were either stained with Coomassie blue or proteins were transferred to nitrocellulose membranes in a Mini Trans-Blot Cell. Membranes were incubated with primary then secondary antibodies diluted in PBS-T and 1% skimmed milk (PBS-TM), which were detected using Amersham ECL Western blot detection method (GE Healthcare). To detect fH binding, blots were incubated in either normal human serum (NHS 1:100), purified (5 µg/ml) or recombinant fH diluted in PBS-TM for two hours, washed then incubated with goat anti-fH pAb (Quidel, 1 in 2,000); membranes were then incubated with murine anti-goat HRP-conjugated IgG (Sigma, 1 in 10,000).

Modification of fHbp and fH

Point mutations in fHbp were introduced by site directed PCR mutagenesis with Roche Expand High Fidelity enzyme or using the QuikChange Site-Directed Mutagenesis Kit (Agilent Technologies) following the manufacturer's protocols, and the primers

```
Stijn-2.P22-S137G/G138D-fwd:
                                  (SEQ ID NO: 7)
CGCTCCTTCCTTGTCGGCGATTTGGGTGGAGAACAT Stijn-2.P22-S137G/G138D-rev:
                                  (SEQ ID NO: 8)
ATGTTCTCCACCCAAATCGCCGACAAGGAAGGAGCG
```

His-tagged proteins were expressed in *E. coli* B834 (DE3) cells and isolated using Ni-NTA Magnetic Agarose Beads (Qiagen) following the manufacturer's protocols and dialysed against 50 mM Sodium acetate, pH 4.5.

DSC Analysis

DSC experiments were carried out using a VP Capillary DSC (GEHealthcare) using a heating rate of 1° C./min from 30 to 110° C. The V2 sample was repeated from 10 to 110° C. when its lower melting event was identified at around 35° C. to ensure that this transition was flanked by sufficient baseline to allow analysis. Samples contained 20 uM of each variant in 25 mM Tris pH7.5, 150 mM NaCl. Samples and buffer were degassed by stirring under vacuum before running. Data analysis was done with the software supplied with the instrument by the manufacturers (Origin version 7.0) with buffer reference subtracted from the sample data and baseline correction.

Proteolytic Cleavage

The sensitivity of WT and mutant (V2MUT) V2 fHbp to proteolytic cleavage was investigated by trypsin digestion. Five µg of fHbp V2 protein was incubated with trypsin ranging from 50 ng to 0.2 ng for 1 h at 37° C. and cleavage was visualised by SDS:PAGE.

REFERENCE

Design and evaluation of meningococcal vaccines through structure-based modification of host and pathogen molecules. Johnson S, Tan L, van der Veen S, Caesar J, Goicoechea De Jorge E, Harding R J, Bai X, Exley R M, Ward P N, Ruivo N, Trivedi K, Cumber E, Jones R, Newham L, Staunton D, Ufret-Vincenty R, Borrow R, Pickering M C, Lea S M, Tang C M. PLoS Pathog. 2012; 8(10):e1002981.

The invention claimed is:

1. A composition comprising:
a modified Variant 2 factor H binding protein (V2 fHbp) having increased stability over a wild type V2 fHbp, wherein the modified variant comprises one or more amino acid substitutions in the N terminal beta barrel of SEQ ID NO: 1 or a V2 fHbp protein with at least 90% identity to SEQ ID NO: 1, wherein the modified variant comprises one or more amino acid substitutions at position 30, 31, 37, 38, 41, 102, 107, 109, 132, and 133 of SEQ ID NO: 1.

2. The composition of claim 1 wherein the maximum value of the left hand peak in a differential scanning calorimetry (DSC) analysis profile of a V2 fHbp is increased by at least 5° C. compared with a wild-type fHbp.

3. The composition of claim 1 wherein the modified variant comprises a mutation at $Ser^{132}$ and $Gly^{133}$.

4. The composition of claim 1 wherein the modified variant comprises $Ser^{132}Gly$ and $Gly^{133}Asp$.

5. The composition of claim 1 wherein the modified variant comprises a mutation at Ser30, Asp102, Ser132 and Gly133; and wherein the mutations comprise $Ser^{30}Gly$, $Asp^{102}Ser$, $Ser^{132}Gly$ and $Gly^{133}Asp$.

6. The composition of claim 1 wherein the modified variant comprises a mutation at Ser30, Leu109, Ser132 and Gly133; and wherein the mutations comprise $Ser^{30}Gly$, $Leu^{109}Phe$, $Ser^{132}Gly$ and $Gly^{133}Asp$.

7. The composition of claim 1, wherein the modified variant comprises a mutation at Ser30, Asp102, Leu109, Ser132 and Gly133; and wherein the mutations comprise $Ser^{35}Gly$, $Asp^{107}Ser$, $Leu^{114}Phe$, $Ser^{137}Gly$ and $Gly^{138}Asp$.

8. The composition of claim 1, wherein the modified variant comprises a mutation at Ser30, Asp102, Val107, Leu109, Ser132 and Gly133; and wherein the mutations comprise $Ser^{30}Gly$, $Asp^{102}Ser$, $Val^{107}Thr$, $Leu^{109}Phe$, $Ser^{132}Gly$ and $Gly^{133}Asp$.

9. The composition of claim 1, wherein the modified variant comprises a mutation at Val107 and Leu109; and wherein the mutations comprise $Val^{107}Thr$, and $Leu^{109}Phe$.

10. An immunogenic composition comprising:
a modified V2 fHbp according to claim 1.

11. The immunogenic composition of claim 10, wherein the composition is capable of eliciting a bactericidal antibody response to N. meningitidis.

12. The immunogenic composition of claim 10 further comprising one or more antigens in addition to the modified V2 fHbp.

13. A therapeutic vaccine directed to N. meningitidis comprising the modified V2 fHbp of claim 1.

14. A pharmaceutical composition comprising:
the modified V2 fHbp of claim 1 and a pharmaceutically acceptable carrier or excipient.

15. A pharmaceutical composition according to claim 1 which is capable of producing a protective immune response to *N. meningitidis*.

* * * * *

SEQUENCE LISTING

<160> NUMBER OF SEQ ID NOS: 8

<210> SEQ ID NO 1
<211> LENGTH: 254
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 2
<211> LENGTH: 254
<212> TYPE: PRT
<213> ORGANISM: Neisseria meningitidis

<400> SEQUENCE: 2

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg

-continued

```
            65                  70                  75                  80
        Gln Ile Glu Val Asp Gly Gln Leu Ile Thr Leu Glu Ser Gly Glu Phe
                            85                  90                  95
        Gln Ile Tyr Lys Gln Asp His Ser Ala Val Ala Leu Gln Ile Glu
                        100                 105                 110
        Lys Ile Asn Asn Pro Asp Lys Ile Asp Ser Leu Ile Asn Gln Arg Ser
                    115                 120                 125
        Phe Leu Val Ser Gly Leu Gly Gly Glu His Thr Ala Phe Asn Gln Leu
        130                 135                 140
        Pro Ser Gly Lys Ala Glu Tyr His Gly Lys Ala Phe Ser Ser Asp Asp
        145                 150                 155                 160
        Pro Asn Gly Arg Leu His Tyr Ser Ile Asp Phe Thr Lys Lys Gln Gly
                        165                 170                 175
        Tyr Gly Arg Ile Glu His Leu Lys Thr Pro Glu Gln Asn Val Glu Leu
                    180                 185                 190
        Ala Ser Ala Glu Leu Lys Ala Asp Glu Lys Ser His Ala Val Ile Leu
                195                 200                 205
        Gly Asp Thr Arg Tyr Gly Gly Glu Glu Lys Gly Thr Tyr His Leu Ala
        210                 215                 220
        Leu Phe Gly Asp Arg Ala Gln Glu Ile Ala Gly Ser Ala Thr Val Lys
        225                 230                 235                 240
        Ile Arg Glu Lys Val His Glu Ile Gly Ile Ala Gly Lys Gln
                        245                 250

<210> SEQ ID NO 3
<211> LENGTH: 254
<212> TYPE: PRT
<213> ORGANISM: Neisseria meningitidis

<400> SEQUENCE: 3

Cys Ser Ser Gly Gly Gly Gly Val Ala Ala Asp Ile Gly Ala Gly Leu
        1               5                   10                  15
        Ala Asp Ala Leu Thr Thr Pro Leu Asp His Lys Asp Lys Ser Leu Gln
                    20                  25                  30
        Ser Leu Thr Leu Asp Gln Ser Val Arg Lys Asn Glu Lys Leu Lys Leu
                35                  40                  45
        Ala Ala Gln Gly Ala Glu Lys Thr Tyr Gly Asn Gly Asp Ser Leu Asn
        50                  55                  60
        Thr Gly Lys Leu Lys Asn Asp Lys Val Ser Arg Phe Asp Phe Ile Arg
        65                  70                  75                  80
        Gln Ile Glu Val Asp Gly Gln Thr Ile Thr Leu Ala Ser Gly Glu Phe
                            85                  90                  95
        Gln Ile Tyr Lys Gln Asn His Ser Ala Val Val Ala Leu Gln Ile Glu
                        100                 105                 110
        Lys Ile Asn Asn Pro Asp Lys Ile Asp Ser Leu Ile Asn Gln Arg Ser
                    115                 120                 125
        Phe Leu Val Ser Gly Leu Gly Gly Glu His Thr Ala Phe Asn Gln Leu
        130                 135                 140
        Pro Asp Gly Lys Ala Glu Tyr His Gly Lys Ala Phe Ser Ser Asp Asp
        145                 150                 155                 160
        Pro Asn Gly Arg Leu His Tyr Ser Ile Asp Phe Thr Lys Lys Gln Gly
                        165                 170                 175
        Tyr Gly Arg Ile Glu His Leu Lys Thr Pro Glu Gln Asn Val Glu Leu
                    180                 185                 190
```

```
Ala Ser Ala Glu Leu Lys Ala Asp Glu Lys Ser His Ala Val Ile Leu
            195                 200                 205

Gly Asp Thr Arg Tyr Gly Gly Glu Glu Lys Gly Thr Tyr His Leu Ala
        210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250
```

<210> SEQ ID NO 4
<211> LENGTH: 254
<212> TYPE: PRT
<213> ORGANISM: Neisseria meningitidis

<400> SEQUENCE: 4

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 5
<211> LENGTH: 254
<212> TYPE: PRT
<213> ORGANISM: Neisseria meningitidis

<400> SEQUENCE: 5

```
Cys Ser Ser Gly Gly Gly Gly Val Ala Ala Asp Ile Gly Ala Gly Leu
1               5                   10                  15
```

```
Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 6
<211> LENGTH: 254
<212> TYPE: PRT
<213> ORGANISM: Neisseria meningitidis

<400> SEQUENCE: 6

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140
```

```
Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165             170                 175

His Gly Lys Ile Glu His Leu Lys Thr Pro Glu Gln Asn Val Glu Leu
            180             185                 190

Ala Ser Ala Glu Leu Lys Ala Asp Glu Lys Ser His Ala Val Ile Leu
            195             200             205

Gly Asp Thr Arg Tyr Gly Gly Glu Glu Lys Gly Thr Tyr His Leu Ala
        210             215             220

Leu Phe Gly Asp Arg Ala Gln Glu Ile Ala Gly Ser Ala Thr Val Lys
225                 230             235                 240

Ile Arg Glu Lys Val His Glu Ile Gly Ile Ala Gly Lys Gln
                245             250

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
cgctccttcc ttgtcggcga tttgggtgga gaacat                          36

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
atgttctcca cccaaatcgc cgacaaggaa ggagcg                          36
```